United States Patent
Johnson et al.

(10) Patent No.: US 10,648,974 B2
(45) Date of Patent: May 12, 2020

(54) ETHYL GLUCURONIDE LATERAL FLOW TEST STRIPS, IMMUNOASSAYS, DEVICES AND METHODS FOR DETECTING OR MEASURING THEREOF

(71) Applicant: CAREHEALTH AMERICA CORPORATION, El Monte, CA (US)

(72) Inventors: Paul Kenneth Johnson, Blue Earth, MN (US); Jacqueline Ann Gale, Basingstoke (GB)

(73) Assignee: CAREHEALTH AMERICA CORPORATION, El Monte, CA (US)

( * ) Notice: Subject to any disclaimer, the term of this patent is extended or adjusted under 35 U.S.C. 154(b) by 0 days.

(21) Appl. No.: 15/314,420

(22) PCT Filed: May 28, 2014

(86) PCT No.: PCT/US2014/039855
§ 371 (c)(1),
(2) Date: Nov. 28, 2016

(87) PCT Pub. No.: WO2015/183266
PCT Pub. Date: Dec. 3, 2015

(65) Prior Publication Data
US 2017/0191996 A1    Jul. 6, 2017

(51) Int. Cl.
*G01N 33/558* (2006.01)
*A61B 10/00* (2006.01)
*G01N 33/98* (2006.01)
*A61B 16/00* (2006.01)
*A61B 5/00* (2006.01)
(Continued)

(52) U.S. Cl.
CPC ......... *G01N 33/558* (2013.01); *A61B 5/6861* (2013.01); *A61B 10/00* (2013.01); *A61B 10/007* (2013.01); *A61B 16/00* (2013.01); *G01N 33/581* (2013.01); *G01N 33/585* (2013.01); *G01N 33/64* (2013.01); *G01N 33/98* (2013.01); *A61B 10/0045* (2013.01); *A61B 2010/0006* (2013.01); *A61B 2010/0009* (2013.01); *G01N 2400/14* (2013.01)

(58) Field of Classification Search
None
See application file for complete search history.

(56) References Cited

U.S. PATENT DOCUMENTS

| 5,747,346 A | 5/1998 | Pullarkat et al. |
| 2006/0240496 A1 | 10/2006 | Anne et al. |

FOREIGN PATENT DOCUMENTS

| CN | 1500212 A | 5/2004 |
| CN | 1818655 A | 8/2006 |
| CN | 201075109 Y | 6/2008 |

(Continued)

OTHER PUBLICATIONS

Rainio, et al. "Immunoassay for ethyl glucuronide in vitreous humor: A new tool for postmortem diagnostics of alcohol use" *Forensic Science International* vol. 226, Nos. 103, pp. 261-265 (2013).

(Continued)

*Primary Examiner* — Christopher L Chin
(74) *Attorney, Agent, or Firm* — Scully, Scott, Murphy & Presser, P.C.

(57) ABSTRACT

Ethyl glucuronide (EtG) lateral flow immunoassay test strips, devices, and methods, useful for testing for alcohol ingestion for alcohol abuse or related diseases and treatment monitoring.

12 Claims, 3 Drawing Sheets

(51) Int. Cl.
    *G01N 33/58*    (2006.01)
    *G01N 33/64*    (2006.01)

(56) References Cited

FOREIGN PATENT DOCUMENTS

| CN | 103267842 A | 8/2013 |
|---|---|---|
| WO | WO 2005098439 A2 | 10/2005 |
| WO | WO 2006073500 A2 | 7/2006 |
| WO | WO 2008/122805 A1 | 10/2008 |
| WO | WO 2013059805 A1 | 4/2013 |

OTHER PUBLICATIONS

Mark, et al. "Microfluidic lab-on-a chip platforms: requirements, characteristics and applications" *Chemical Society Reviews* vol. 39, No. 3, pp. 1153-1182 (2010).

ETHYL GLUCURONIDE LATERAL FLOW TEST STRIPS, IMMUNOASSAYS, DEVICES AND METHODS FOR DETECTING OR MEASURING THEREOF

FIELD OF THE INVENTION

The present invention relates to Ethyl glucuronide ("EtG") lateral flow immunoassay test strips, devices, and methods, useful for alcohol ingestion for alcohol abuse or abstinence testing or monitoring, or related diseases and treatment monitoring.

BACKGROUND

Immunoassays are becoming increasingly popular as methods for detecting or monitoring the presence of drugs or analytes in body fluids or biological samples. A particular challenge in the development of immunoassays is the production of an antibody to the target drug/analyte since many are not inherently antigenic. Generally, the drug must be modified to make an antigenic derivative, yet the antibody produced to the antigenic derivative must be able to recognize the drug as it is contained in the fluid specimen to be tested with an appropriately useful degree of sensitivity, generally a level with physiological and/or pharmacological significance. Sensitivity is not the only concern. Often a variety of metabolites exist and other drugs may be present along with the target analyte. Preferably, an antibody to a particular drug or metabolite has minimal, if any, cross-reactivity with other metabolites or other drugs.

Lateral flow tests, also known as Lateral Flow Immunochromatographic Assays, are devices intended to detect the presence (or absence) of a target metabolite in sample (matrix) without the need for specialized and costly equipment, though many lab based applications exist that are supported by reading equipment. Typically, these tests are used for medical diagnostics either for home testing, point of care testing, or laboratory use, as well as law enforcement testing of drivers of vehicles.

The technology is based on a series of capillary beds, such as layers of porous paper or sintered polymer. Each of these layers has the capacity to transport fluid (e.g., urine) spontaneously. A first layer, (the sample pad) acts as a sponge and holds an excess of sample fluid. Once soaked, the fluid migrates to the second layer (conjugate pad) in which the manufacturer has stored the so-called conjugate, a dried format of bio-active compounds (see below) in a salt-sugar matrix that contains a complete reagent mixture needed to guarantee an optimized chemical reaction between the target molecule (e.g., an antigen) and its chemical partner (e.g., a primary antibody) (optionally a second, labeled antibody (secondary antibody) (e.g., sandwich assay) that has been immobilized on the particle's surface. While the sample fluid dissolves the salt-sugar matrix, it also dissolves the reagents and in one combined transport action the sample and reagents mix while flowing through the porous structure. In this way, the metabolite binds to the antibodies while migrating further through the third capillary bed. This bed has one or more areas (often called stripes) where a third molecule (usually a labeled antibody) has been immobilized by the manufacturer. By the time the sample-conjugate mix reaches these stripes, the metabolite has been bound on the first antibody and the third 'capture' molecule binds the complex. After a while, when more and more fluid has passed the stripes, antibody/metabolite complex accumulate and the striped-area changes color. Typically there are at least two stripes: one (the control) that captures any particle and thereby shows that reaction conditions and technology worked. The second striped-area contains a specific capture molecule and only captures those complexes comprising the metabolite molecule and the first antibody. After passing these reaction zones, the fluid enters the final porous material, the wick, that provides the oncotic pressure that draws the test fluid through the multiple capillary beds and acts as a waste container.

Lateral Flow Tests can operate as either competitive or sandwich assays. In a competitive assay, the complex is rinsed, the antibody is limited or there is a target analog that competes with the target for primary antibody binding. In a sandwich assay, a primary antibody is used which is specific to the antigen and a secondary antibody is located in the third layer, the secondary antibody specific only to the first antibody. When a secondary antibody is used, it may be conjugated to a visual (or visualizable) label such as a fluorophor or an enzyme specific to a visualized chromophor.

Ethyl glucuronide ("EtG"), which is shown in FIG. 3, is a direct metabolite of ethyl alcohol formed by the conjugation of ethanol with activated glucuronic acid in the presence of UDP glucuronyl transferase on mitochondrial membranes. While ethanol is detectable for only a few hours after consumption, EtG is detectable for up to about four or five days after alcohol consumption, making it a reliable target analyte for determining alcohol consumption, assuming that the test can be validated and controlled for false positive and false negatives. Monitoring of alcohol consumption is important for many reasons including use in conjunction with alcohol abuse and abstinence testing and monitoring (for one or more of medical treatment, and court or law enforcement testing and monitoring), safety-sensitive programs such as airline pilots and health care or emergency care professionals, as well as operators of heavy machinery or vehicles.

Currently, EtG is accurately and reproducibly detected by gas chromatography/mass spectrometry ("GC/MS") and liquid chromatography/tandem mass spectrometry ("LC/MS/MS"). An enzyme linked immunoassay ("ELISA") test to detect EtG using a polyclonal antiserum has been attempted, but the use of polyclonal antibodies can result in an significant and increased number of false positives and false negatives, which indicates poor specificity, and sensitivity of the assay. Additionally, exposure to external ethanol (e.g., personal care products, first aid products, cleaning products, and the like that contain ethanol also produces false positives. This inaccuracy has led to recommendations or policies that only high levels of EtG (e.g., at least 500, 750, or 1000 ng/mL of urine) are acceptable for a positive test result, which can result in a significant number of false negatives, especially using immunoassay testing for EtG. Accordingly, no product appears to be on the market to provide the advantages of an accurate, reproducible, and commercially viable immunoassay for EtG, that optionally does not require further validation by the use of additional testing including ("GC/MS") and liquid chromatography/tandem mass spectrometry ("LC/MS/MS"). Such tests also require a significant amount of time to provide results, e.g., at least hours, days, or weeks.

Therefore, there is a need or provide and solve one or more of the current problems related to developing devices and methods for an accurate, reproducible, and commercially viable immunoassay for EtG, e.g., that provides one or more of better sensitivity and/or specificity (e.g., with the use of EtG-specific monoclonal antibodies), lower and/or acceptable rates of false negatives and/or false positives, that does not require a second round of testing to confirm positive test using a much more expensive and time consuming and laboratory required test (e.g., GC/MS and/or LC/MS/MS), as compared to prior assays. Accordingly, there is also a need for systems and methods of making that provide improvements over known systems or methods that optionally overcome one or more of these problems.

SUMMARY

Non limiting embodiments of the present invention can optionally include one or more of EtG immunoassay lateral flow test strips, devices, methods, and/or reagents, such as EtG specific lateral flow strip immunoassay devices and methods of making and using thereof.

Non limiting optional embodiments can include devices, methods of making or using, software, computer readable computer systems, and/or systems for testing for or detecting the presence of drugs or other chemicals or metabolites, e.g., but not limited to, diagnosing, monitoring, or measuring chemical or other parameters relating to disease or medical conditions, or for testing for illegal or prohibited drugs, optionally in non-controlled or difficult to control environments.

A device, method or system of the invention can optionally use one or more of tissue or bodily fluids (e.g., but not limited to, urine, blood, saliva, or plasma) as the test sample for detecting EtG. Non limiting optional embodiments can optionally include one or more of an electronic device such as a smart phone or other wireless, internet or cellular communications capable device, in combination with digital and/or other imaging, data processing, data storage and/or wireless electronic transmission of data via cellular networks or Wi-Fi.

A device, system or method can optionally collect, detect, process, manipulate, alter, condition, determine, validate, and/or test urine, oral or other bodily fluids or tissues in volumes sufficient for testing, chemically and/or mechanically collecting, detecting, processing, manipulating, altering, conditioning, determining, validating, and/or testing for EtG in one or more of urine or an oral or other bodily fluid or tissue. A device, system or method can further provide for the set up and/or optimize for testing and/or delivering the conditioned fluids to lateral flow test strips or other testing systems for diagnosing, monitoring, or measuring chemical or other parameters relating to disease or medical conditions, or for determination of the presence or absence, or other quantitative or qualitative measurement, of EtG.

Such devices can also optionally provide for timing the test endpoint and/or subsequent image capture by either automatic initiation of timing once the testing device is inserted into the positioning case of by the user initiating the start time of the test by interacting with a touch sensitive or other graphical user interface.

A lateral flow test strip device, system or method can optionally provide wherein the person performing the test (tester) performs at least one selected from the group consisting of removing the test device from the packaging, removing a cap from an fluid collecting device or placing urine or other bodily fluid in the fluid collecting device or on the test strip or testing device (e.g., but not limited to, a test strip holder, cassette, insert, testing device component, and the like).

The test strip, device, or system can optionally include an ethyl glucuronide (EtG) lateral flow test strip immunoassay system, device or method for detecting ethyl glucuronide in urine or other bodily fluid (e.g., saliva, blood, blood component, or other tissue sample (e.g., skin, hair or nails), comprising at least one or more of:

(a) a lateral flow test strip as schematically shown in FIGS. 1 and 2, the test strip comprising;
(i) at least one type of capillary flow material capable of reproducibly providing lateral flow of a urine, bodily fluid or tissue sample through the test strip to reproducibly interact and detect EtG using a detectably labeled EtG-specific antibody and a first and a second detectable label comprised in the test strip, the system providing (1) a positive result, with a (C) colored band only developing as shown in FIG. 2; (2) a negative result, with both the (T) colored band and a (C) colored band developing as shown in FIG. 2; or an invalid result, with only the (T) colored band developing as shown in FIG. 2, or no band;
(ii) a urine/bodily fluid/tissue sample or control sample application area (A), as shown in FIG. 1, comprising a sample application component;
(iii) a labeled EtG labeled antibody area (B), as shown in FIG. 1, comprising a detectably labeled EtG specific antibody provided in or to the test strip material, the detectably labeled EtG specific antibody comprising an EtG specific antibody conjugated to a detectable label component and soluble in or conducted along the test strip by capillary action of the urine, bodily fluid or tissue or control sample after application to the test strip;
(iv) a first detection area (D) comprising the first detectable label as a first labeled moiety that binds the detectably labeled EtG specific antibody, when the concentration of EtG in the urine, bodily fluid or tissue or control sample is below a pre-selected threshold value between 100 and 2000 ng/mL; wherein the binding of the detectably labeled EtG specific antibody below the pre-selected threshold results in the negative result with both the (T) and (C) colored bands as shown in FIG. 2; and wherein the detectably labeled EtG specific antibody does not detectably or significantly bind the first detectable label and also does not provide the negative result, when the EtG in the urine, bodily fluid or tissue or control sample is above the pre-selected threshold value;
(v) a second detection area (E) comprising the second detectable label as a second labeled moiety that binds the detectably labeled EtG specific antibody, when the concentration of the EtG in the urine, bodily fluid or tissue or control sample is above the pre-selected threshold value between 100 and 2000 ng/mL; and wherein the binding of the detectably labeled EtG specific antibody above the pre-selected threshold results in the positive result with only the (C) colored band as shown in FIG. 2; and wherein the detectably labeled EtG specific antibody does not detectably or significantly bind the first detectable label, when the EtG in the urine, bodily fluid or tissue or control sample is above the pre-selected threshold value; and
wherein, when assay is invalid, the binding of the detectably labeled EtG specific antibody results in the invalid result with only the (T) colored band as shown in FIG. 2, or no bands; and wherein the detectably labeled EtG specific antibody does not detectably or significantly bind the second detectable label.

Optionally, one or more of the following can be included: wherein: the threshold is 500, 750, or 1000 ng/mL; the detectable label is colloidal or latex gold; the EtG specific antibody is monoclonal; the affinity of the EtG specific antibody for EtG is at least $10^{-7}$ $K_D$; the detectable label is comprised of an enzyme, enzyme fragment or enzyme donor fragment.

The method can optionally include one or more of the steps of: providing a lateral flow test strip as schematically shown in FIGS. 1 and 2; applying the urine, bodily fluid or tissue or control sample to the test strip; and determining whether the urine, bodily fluid or tissue or control sample comprises EtG above or below the threshold.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DESCRIPTION

Figure 3:
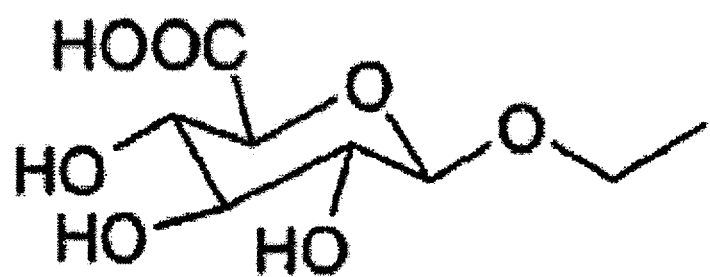
FIG. 3 illustrates the chemical structure of ethyl glucuronide.

Ethyl glucuronide ("EtG"), which is shown in FIG. 3, is a direct metabolite of ethyl alcohol formed by the conjugation of ethanol with activated glucuronic acid in the presence of UDP glucuronyl transferase on mitochondrial membranes. While ethanol is detectable for only a few hours after consumption, EtG is detectable for up to four or five days after alcohol consumption, making it a reliable target analyte for determining alcohol consumption. Monitoring of alcohol consumption is important for many reasons including use in conjunction with alcohol abuse and abstinence testing and monitoring (for one or more of medical treatment, and court or law enforcement testing and monitoring), safety-sensitive programs such as airline pilots and health care or emergency care professionals, as well as operators of heavy machinery or vehicles.

Currently, EtG is detected by gas chromatography/mass spectrometry ("GC/MS") and liquid chromatography/tandem mass spectrometry ("LC/MS/MS"). Such methods are time-consuming and expensive. Zimmer et al. (J. Analytical Toxicology, 26:11-16, 2002; incorporated herein in its entirety) describes an enzyme linked immunoassay ("ELISA") or enzyme immunoassay (EIA) test to detect EtG using a polyclonal antiserum induced by immunization with EtG linked directly to peroxidase enzyme via the carboxyl group at position 5 of EtG. The use of polyclonal antibodies can result in an increased number of false positives (23.2%) and false negatives (24.3%), which indicates poor specificity, and sensitivity of the assay. In 2001, Mediagnost Company Ltd. (Reutlingen, Germany) began development of an ELISA test utilizing monoclonal antibodies prepared by immunization with a lipopeptide conjugate of EtG (Wurst et al., Addiction 98(Suppl. 2), pages 51-61, 2003). However, to date, no product has been made available.

Generally, the present invention can optionally include one or more of improved EtG immunoassay lateral flow test strips and devices and methods, including providing antibodies for use as components of EtG specific immunodiagnostic reagents and in immunodiagnostic protocols. As such, the present invention can optionally include improved EtG-based immunogens, EtG-based antigens, antibodies prepared from EtG-based immunogens, and methods of making and using the same. More particularly, the present invention can optionally include improved immunoassay lateral flow test strips, devices, and techniques that can be used with the EtG specific antibodies, prepared from EtG-based immunogens, in accordance with the present invention.

In non-limiting embodiments, the present invention can optionally include an antibody prepared with an EtG-based immunogen, wherein the antibody is an anti-EtG antibody capable of interacting with EtG and the EtG analog. Also, the antibody can be capable of interacting with EtG in a sample at a concentration of less than or equal to about 0.05 mg/dL, and have a cross-reactivity of less than about 1% with at least one of ethyl glucuronide, lorazepam glucuronide, oxazepam glucuronide, temazepam flucuronide, D-glucose, 1-butanol, or 2-butanol.

In non-limiting embodiments, the present invention can optionally include an immunoassay system for detecting EtG, wherein the system can have an anti-EtG antibody prepared with an EtG-based immunogen described herein. Also, the immunoassay system can have an EtG-based immunoassay reagent.

In non-limiting embodiments, the present invention can optionally include a method of detecting EtG in a sample. Such a method can include the following: obtaining a sample from a subject suspected of consuming ethyl alcohol; combining an anti-EtG antibody and an EtG analog with the sample to form a first composition, said antibody and analog being free within the first composition, and said antibody being capable of binding EtG and the EtG analog; allowing any free EtG from the sample and the EtG analog to compete for binding with the antibody; and detecting binding between the EtG analog and the antibody. By being free, the antigen and antibody are capable of freely moving within a solution so as to be solubilized or suspended, rather than being attached to the reaction vessel as in ELISA assays. The anti-EtG antibody can be prepared with an EtG-based immunogen as described herein. The EtG analog can be prepared as described herein to include a detectable label, such as an enzyme (e.g., G6PDH), enzyme fragment or enzyme donor fragment (e.g., the .beta.-galactosidase enzyme donor fragment ED28 and n is about 2).

Ethyl glucuronide (EtG) is a minor nonoxidative metabolite of ethyl alcohol formed by the in vivo conjugation of ethanol with glucuronic acid with UDP glucuronosyl transferase. ETG is a product of the metabolic process of ingested alcohol (ethanol), which is rapidly metabolized in the body, and which is also excreted in the blood, hair and urine. By using an ETG Rapid Test Device, ETG can be detected in the urine, confirming the consumption of alcohol. The ETG metabolite remains in the body longer and therefore has a more useful window of detection of 8 to 80 hours. ETG testing according the invention is an excellent option, e.g., but not limited to, zero-tolerance alcohol consumption or rehabilitation programs.

A non limiting embodiment of the invention can include an EtG lateral flow immunoassay test strip and/or device, e.g., an ETG Rapid Test Device (Urine) that was designed to detect ETG through visual interpretation of color development in the Device which detection is mediated by the use of EtG specific antibodies that have been labeled for detection. The membrane or similar component of the test strip can be immobilized with ETG conjugates on the test region, and the conjugate pad can optionally be pre-coated with colored or labeled anti-ETG antibodies, e.g., but not limited to, colloidal or latex gold labeled EtG antibody (e.g., monoclonal or polyclonal, or an EtG binding fragment thereof) conjugates. The antibodies can optionally not be provided on the conjugate pad, but optionally can include where instead the gold is put directly onto a plastic device, dried, the specimen added to the gold to allow dissolution and then the gold and specimen are mixed to then flow up a strip comprised of bottom pad/sample pad, membrane and wicking material/pad. After specimens were added, (e.g., urine, bodily fluid or tissue and controls, e.g., positive and/or negative controls) the gold conjugates moved along the membrane or test strip (e.g., chromatographically by capillary action) and the antibodies migrate to the test region. If there is no drug molecule (i.e., EtG) in the urine, then the antibody-gold conjugate attaches to the drug conjugate to form a visible line in the test region, where the formation of a visible precipitant in the test region occurs when the urine, bodily fluid or tissue is negative for the drug. If ETG is present in the urine, the drug antigen competes with the immobilized drug conjugate on the test region for limited antibody sites. Optionally, the EtG can be detected using a sandwich assay using a second labeled antibody to detect the first antibody, as known in the art. In case of sufficient concentration of the drug metabolite EtG, it fills the limited antibody binding sites. This will prevent attachment of the colored antibody-colloidal or latex gold conjugate to the drug conjugate zone on the test region. Therefore, absence of the colored band on the test region indicates a positive result. Appearance of a colored band at the control region serves as a procedural control. This indicates that proper volume of specimen has been added and membrane wicking has occurred.

During testing, a portion of the urine, bodily fluid or tissue specimen migrates upward by capillary action. EtG, if present in the urine, bodily fluid or tissue below its cut-off concentration, will not saturate the binding sites of its specific antibody. The antibody will then react with the drug-protein conjugate and a visible colored line will show up in the test line region of the specific drug strip. The presence of drug above the cut-off concentration in the urine, bodily fluid or tissue or oral fluid specimen will saturate all the binding sites of the antibody. Therefore, the colored line will not form in the test line region. A drug-positive urine, bodily fluid or tissue specimen will not generate a colored line in the specific test line region of the strip because of drug competition, while a drug-negative urine, bodily fluid or tissue or oral fluid specimen will generate a line in the test line region because of the absence of drug competition.

To serve as a procedural control, a colored line will always appear at the control line region, indicating that proper volume of specimen has been added and membrane wicking has occurred.

Figure 1:
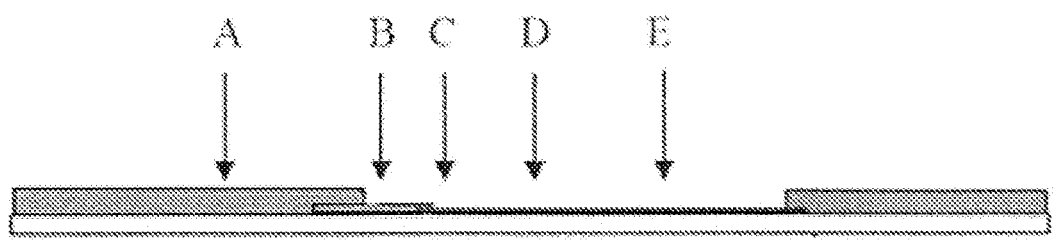
FIG. 1 shows a schematic representation of a non-limiting example of a test strip of the invention.

As shown in FIG. 1, the specimen is added at the sample application region, e.g., (A), and then migrates via capillary action along the membrane or test strip to interact with the labeled conjugate (B) which can be provided in alternative labeled forms. EtG present in the specimen (e.g., urine or other bodily fluid or tissue) below cutoff or threshold amounts (e.g., less than 100, 200, 250, 300, 350, 400, 450, or 500, 600, 700, 750, 800, 900, 1000, 1100, 1200, 1300, 1400, 1500, 1700, 1750, 1800, 1900, or 2000 ng/mL), will not saturate all of the binding sites of the gold-conjugated anti-EtG antibodies and will not form a colored antibody-antigen complex (C). The gold-conjugated antibodies will then be captured by immobilized conjugate and a visible (e.g., red) band will form indicating a negative result at position (D) (corresponding to (T) in FIG. 2 below, where the gold-EtG antibody complex will bind at (D) since the EtG binding sites on the EtG antibody are not saturated and will bind EtG or epitope or a mimetic thereof immobilized at (D) to provide a labeled negative result and band at (D) (corresponding to band (T) in FIG. 2. The absence of line formation in the test line region indicates a positive reading and that the (A) level of the test specimen is above the detection sensitivity of the test (e.g., one of 100, 200, 250, 400, or 500, 600, 700, 750, 800, 900, 1000, 1100, 1200, 1300, 1400, 1500, 1700, 1750, 1800, 1900, or 2000 ng/mL, where 500, 750, or 1000 ng/mL is preferred).

Figure 2:
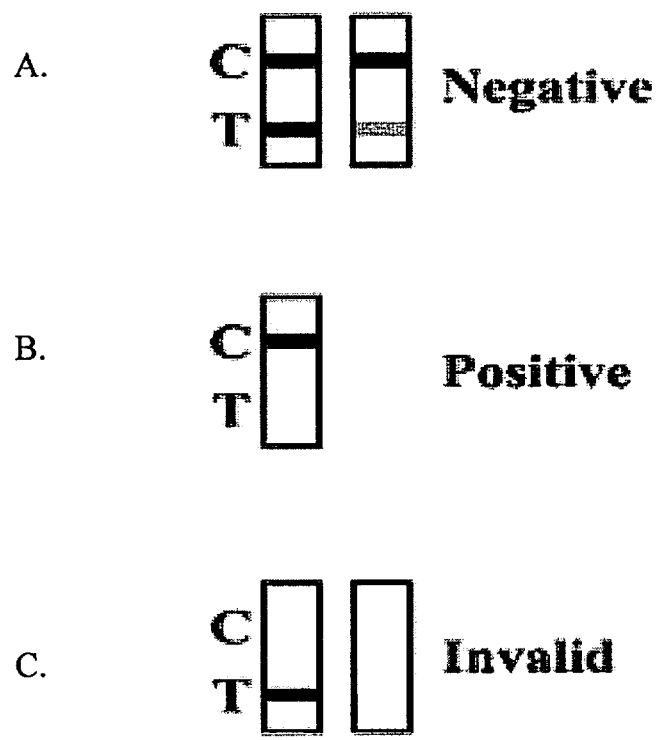
FIG. 2 shows a schematic representation of a non-limiting example of a test strip of the invention showing negative, positive and invalid results.

In the control line region of the membrane, immobilized reagents capture colored conjugate regardless of the presence of the test specimen composition. The resulting visible red band (E) confirms that the assay is functioning correctly. FIG. 2 illustrates in a non-limiting example one set of the possible outcomes of the test.

The test strip, device, or system can optionally include an ethyl glucuronide (EtG) lateral flow test strip immunoassay system, device or method for detecting ethyl glucuronide in urine, comprising at least one or more of:

(a) a lateral flow test strip as schematically shown in FIGS. 1 and 2, the test strip comprising;
  (i) at least one type of capillary flow material capable of reproducibly providing lateral flow of a urine, bodily fluid or tissue sample through the test strip to reproducibly interact and detect EtG using a detectably labeled EtG-specific antibody and a first and a second detectable label comprised in the test strip, the system providing (1) a positive result, with a (C) colored band only developing as shown in FIG. 2; (2) a negative result, with both the (T) colored band and a (C) colored band developing as shown in FIG. 2; or an invalid result, with only the (T) colored band developing as shown in FIG. 2, or no bands;
  (ii) a urine, bodily fluid or tissue or control sample application area (A), as shown in FIG. 1, comprising a sample application component;
  (iii) a labeled EtG labeled antibody area (B), as shown in FIG. 1, comprising a detectably labeled EtG specific antibody provided in or to the test strip material, the detectably labeled EtG specific antibody comprising an EtG specific antibody conjugated to a detectable label component and soluble in or conducted along the test strip by capillary action of the urine, bodily fluid or tissue or control sample after application to the test strip;
  (iv) a first detection area (D) comprising the first detectable label as a first labeled moiety that binds the detectably labeled EtG specific antibody, when the concentration of EtG in the urine or control sample is below a pre-selected threshold value between 100 and 2000 ng/mL; wherein the binding of the detectably labeled EtG specific antibody below the pre-selected threshold results in the negative result with both the (T) and (C) colored bands as shown in FIG. 2A; and wherein the detectably labeled EtG specific antibody does not detectably or significantly bind the first detectable label and also does not provide the negative result, when the EtG in the urine, bodily fluid or tissue or control sample is above the pre-selected threshold value;

(v) a second detection area (E) comprising the second detectable label as a second labeled moiety that binds the detectably labeled EtG specific antibody, when the concentration of the EtG in the urine, bodily fluid or tissue or control sample is above the pre-selected threshold value between 100 and 2000 ng/mL; and wherein the binding of the detectably labeled EtG specific antibody above the pre-selected threshold results in the positive result with only the (C) colored band as shown in FIG. 2B; and wherein the detectably labeled EtG specific antibody does not detectably or significantly bind the first detectable label, when the EtG in the urine, bodily fluid or tissue or control sample is above the pre-selected threshold value; and wherein, when assay is invalid, the binding of the detectably labeled EtG specific antibody results in the invalid result with only the (T) colored band or no bands, as shown in FIG. 2C; and wherein the detectably labeled EtG specific antibody does not detectably or significantly bind the second detectable label.

Optionally, one or more of the following can be included: wherein: the threshold is 500, 750, or 1000 ng/mL; the detectable label is colloidal or latex gold or an ELISA or EIA label; the EtG specific antibody is monoclonal or polyclonal; the affinity of the EtG specific antibody for EtG is at least 1, 2, 3, 4, 5, 6, 7, 8, or 9 times one or more of $10^{-5}$ $K_D$, $10^{-6}$ $K_D$; $10^{-7}$ $K_D$; $10^{-8}$ $K_D$; or $10^{-9}$ $K_D$; the detectable label is comprised of an enzyme, enzyme fragment or enzyme donor fragment, and/or a detectable labels. Non limiting examples of enzymes used in ELISAs or EIAs, as well known in the art, include horseradish peroxidase (HRP), alkaline phosphatase (AP) or glucose oxidase, or streptavidin/biotin. These enzymes allow for detection often because they produce an observable color change in the presence of certain reagents. See, e.g., "The Immunoassay Handbook", 3rd Edition, David Wild, Ed., Elsevier, 2008, entirely incorporated herein by reference.

The method can optionally include one or more of the steps of: providing a lateral flow test strip as schematically shown in FIGS. 1 and 2; applying the urine, bodily fluid or tissue or control sample to the test strip; and determining whether the urine, bodily fluid or tissue or control sample comprises EtG above or below the threshold.

In non-limiting embodiments, the present invention can optionally include an immunoassay for determining the presence and/or amount of EtG in a sample (e.g., urine, e.g., at least 100, 200, 250, 300, 350, 400, 450, 500, 600, 700, 800, 900 or 1000 ng/mL of urine, or more, or any range or value therein) with suitable specificity and sensitivity (e.g., affinity, on-rate, off-rate, avidity, $K_D$, and the like).

In non-limiting embodiments of the present invention, EtG can be chemically modified to produce immunogens that are capable of inducing an immunologic response in a mammal so as to produce an anti-EtG antibody. Also, the EtG can be chemically modified to produce antigens that are capable of interacting with the anti-EtG antibodies. Additionally, the EtG can be chemically modified to produce conjugates that include the EtG bound to a label that are also capable of interacting with the anti-EtG antibodies.

In another embodiment of the present invention, an EtG-based immunogen can be used to produce an anti-EtG antibody with specificity and sensitivity for EtG. Also, the anti-EtG antibody directed to EtG can be used in connection with an immunoassay to detect the presence and/or determine the concentration of EtG in a sample, such as a patient specimen. Moreover, anti-EtG antibodies prepared from EtG-based immunogens can be combined in a system or kit for detecting the presence and/or determining the concentration of EtG in samples, such as urine.

In accordance with one embodiment of the present invention, the methods for making the anti-EtG antibodies (e.g., monoclonal and/or polyclonal) prepared from EtG-based immunogens or immunogenic derivatives of EtG are well known in the art and/or as described or referenced herein.

Definitions:

Unless stated otherwise, the following terms and phrases have the meanings provided below.

As used herein, the term "affinity" is meant to refer to a measure of the strength of binding between an epitope and an antibody. Accordingly, a single antibody can have a different affinity for various epitopes. This can allow a single antibody to bind strongly to one epitope and less strongly to another.

As used herein, the terms "analog" or "derivative" are meant to refer to a chemical compound or molecule made from a parent compound or molecule by one or more chemical reactions. As such, an analog can be a compound with a structure similar to that of EtG or based on an EtG scaffold, but differing from it in respect to certain components or structural makeup, which may have a similar or opposite action metabolically. An analog or derivative of EtG in accordance with the present invention can be used to compete for binding with an antibody that recognizes both the analog and EtG. Also, an analog can include an operative moiety coupled to EtG through a linker group.

As used herein, the term "antibody" is meant to refer to polyclonal and/or monoclonal antibodies and related antigen recognition units, including fragments and derivatives of immunoglobulin molecules, as known in the art (e.g., one or more of variable, constant or linking regions, heavy chain and/or light chain, CDRs 1, 2 and/or 3, and the like, as well as fusion proteins thereof, e.g., PEGylated, conjugated, etc., as known in the art). Any known method can be used, e.g., isolation and cloning from B-cells of immunized animals (e.g., mice, rat, etc.), recombinant methods, e.g., phage display, transgenic mice, chimeric, and the like, which can optionally use protein A for binding the antibody and/or in place of the gold label optionally used on the test strip). One method of producing antibodies using immunized animals is to administer an immunogenic derivative of the target analyte, generally combined with an adjuvant such as Freund's adjuvant, in a series of injections to a host animal for the purpose of inducing an immunologic response, and then isolating and cloning the antibody producing B-cells from the animal's spleen or blood. Such methods are well known to those skilled in the art. Methods for producing monoclonal antibodies were first described by Kohler and Milstein (Nature, Vol. 256, pp 495-497, 1975; incorporated herein in its entirety) and have been modified several times since the appearance of that publication. For hybridoma technology, the reader is directed generally to U.S. Pat. Nos. 4,491,632; 4,472,500; and 4,444,887; and Methods in Enzymology, 73B:3 (1981); each is incorporated herein in its entirety. Since the particular method is not critical, any proven method can be used to produce an antibody using immunogens as described herein, as selected for the desired properties, e.g., specificity, affinity, on rate, off rate, $K_D$, and the like. As used herein, the term "antibody" is meant to refer to a protein that is produced in response to the presence of foreign molecules in the body. They can be characterized by their ability to bind both to antigens and to specialized cells or proteins of the immune system. For example, antibodies are divided into five classes, IgG, IgM, IgA, IgE, and IgD, and are immunoglobulin produced by plasma cells.

As used herein, the terms "carrier," "immunogenic moiety," or "immunogenic carrier," are meant to refer to an immunogenic substance, commonly a protein, which can be coupled to a hapten. An immunogenic moiety coupled to a hapten can induce an immune response and elicit the production of antibodies that can bind specifically with the hapten. Immunogenic moieties are operative moieties that include proteins, polypeptides, glycoproteins, complex polysaccharides, particles, nucleic acids, polynucleotides, and the like that are recognized as foreign and thereby elicit an immunologic response from the host. Examples of polysaccharides are starches, glycogen, cellulose, carbohydrate gums such as gum arabic, agar, and so forth. The polysaccharide can also contain poly(amino acid) residue and/or lipid residues. Some of the most common carrier proteins in use today are keyhole limpet hemocyanin ("KLH," MW 450,000 to 13,000,000), egg ovalbumin, bovine gamma-globulin ("BGG"), and bovine serum albumin ("BSA," MW 67,000).

As used herein, the term "epitope" is meant to define the region of an antigen that interacts with an antibody. Accordingly, a molecule or other substance, which is an antigen, can include at least one epitope with antibody activity. This can allow for an antigen to have various epitopes recognized by the same or different antibody. Also, an epitope is not an intrinsic property of any particular structure, but can be defined as a binding site that interacts with the antibody.

As used herein, the term "hapten" is meant to refer to a partial or incomplete antigen. They are protein-free substances, mostly low molecular weight substances, that are not capable of stimulating antibody formation, but which do react with antibodies, formed by coupling the hapten to a high molecular weight carrier and then injecting the coupled product, i.e., immunogen, into a human or other animal subject.

As used herein, the terms "immunoassay" or "immunodiagnostic" are meant to refer to techniques that make use of the binding between an antigen and an antibody in order to identify and/or quantify at least one of the specific antigen or specific antibody in a biological sample. Examples of immunoassay can include the following: (1) antibody capture assays; (2) antigen capture assays; (3) two-antibody sandwich assays; and (4) detectable antigen-antibody interactions. Additionally, it is contemplated that new immunoassays will be developed and will be capable of employing the analogs and antibodies of the present invention.

As used herein, the terms "label," "detector molecule," or "tracer" are meant to refer to any molecule which produces, or can be induced to produce, a detectable signal. The label can be conjugated directly or via a linker to an analyte, immunogen, antibody, or to another molecule such as a receptor or a molecule that binds to a receptor, such as a ligand. Non-limiting examples of labels, detector molecules, or tracers include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, hapten radioactive isotopes, and the like. As described herein, the analogs can also be coupled to a variety of labels by methods well known in the art to provide a variety of reagents useful in various immunoassay formats. For detecting the results of the immunoassays, detector molecules such as fluorophores, for example, fluorescein, radio-labels, or chemiluminescent groups can be coupled to the analogs to produce tracers.

As used herein the term "operative moiety" is meant to refer to a molecule or macromolecule coupled to EtG through a linker group. Also, an operative moiety provides an operative function to the EtG for use in preparing or performing immunodiagnostic assays. An operative group can include immunogenic moiety, antigen moiety, tracer moiety, and the like. Usually, an operative group is illustrated as "Z" in the chemical formulas provided below.

As used herein, the terms "sample" or "biological sample" are meant to refer to any quantity of a substance from a living thing, including humans. Such substances include, but are not limited to, blood, serum, urine, tears, cells, organs, tissues, and hair.

Additionally, the terms used herein to describe the invention can be construed using the foregoing definitions and/or definitions well known in the art. As such, the foregoing terminology is meant to describe the invention and is not intended to be limiting.

The present disclosure is directed, in general, to methods of making, providing and/or using portable lateral flow test strip systems, devices, or methods, saliva or body fluid lateral flow test strip systems, devices or methods, optional testing cartridges, systems, optionally made using one or more press manufacturing methods, devices, and/or systems, as further described herein, and/or as known in the art.

It has been unexpectedly discovered that one or more aspects of the design, content, components, orientations, compression, adhesives, plastics, roller systems and methods, contacts, fluidic contacts, shapes, sizes, dimensions, holes, cutting, slits, overlays, venting, timing, control, and/or other aspects of the materials, components, manufacturing methods and structures, provide test strips with results that are unexpected, synergistic, taught away from, advantageous, lower cost, more accurate, more reproducible, more consistent, provide precise volume control and/or accuracy, provide more reproducible and accurate results at lower cost and/or faster production, as described herein optionally with what is known in the art.

Non limiting optional embodiments of the present invention are based the discovery and engineering of improved test strips and manufacturing methods as described herein and known in the art. It has unexpectedly been found, or taught away from, including but not limited to, one or more the following, as non limiting examples:

Capillary force driven—Capillary force driven migration has been discovered to be controlled by one or more of opening or closing an external vent that can be manufactured and controlled using a new process as described herein in combination with what is known in the art. As a closed vent will cause air pressure to build in the device as fluid flows in thus displacing the air in the sealed chamber, opening to an external vent releases this pressure enabling flow to continue, while automatic closing can be accomplished by position vents at positions where the sample fluid flow is stopped as desired and calibrated positions to provide one or more of accuracy, consistency, pre-calibration, faster manufacture, or cheaper manufacture; Dissolvable membranes can be employed to stop flow until the membrane dissolves to provide one or more of accuracy, consistency, pre-calibration, faster manufacture, or cheaper manufacture. As a non-limiting example, such a vent can be designed and/or made to close an air passage when wetted since the air pressure generated within a compartment by capillary force driven liquid flow low enough so as to not be sufficient to force air through a wet material, wherein this can be used to stop flow passively and automatically at a time determined only by the flow rate of a fluid moving towards a valve and the distance on flow. Such features can optionally be used as a fluidically controlled stop or start switch.

Passive volume control: Capillary driven fill can be governed by size of the materials that exhibit capillary forces towards aqueous materials; The volume of the materials can be very tightly controlled the height of the compartment that the material resides in since this laminated assembly has very precise vertical dimensionality, e.g., within at least one of 0.1-5 percent variation; Flow stops when the materials are saturated with fluid; Materials are surrounded by hydrophobic materials to ensure there is on flow outside the materials that support capillary force driven flow.

Fluidic contacts between materials can be made by placing holes in the laminated liquid tight layers instead of the typical overlapping approached used for lateral flow rapid test strips yielding more precise fluid transfer volumes. When the flow is directed to move from a transport material positioned below a second transport material and these two materials are connected by a hole in one of the laminated layers, this ensures that all flow is driven by capillary forces and not by fluidic head pressure. Fluid can be made to enter a transport material at very precise locations as opposed to dipping a test strip in a fluid.

Labeling can be registered to critical components within the assembled device. This significantly minimizes registration errors.

Open space compartments with hydrophilic surfaces can be designed into the device. These are essentially capillary tubes. These spaces fill from the point of sample application to the most distal portion. When the test strip or other fluidic components are positioned at the distal end of this channel, this channel serves as a fluidic metering device thus ensuring that a testing process will not begin until the channel is full and there is sufficient sample volume to complete a testing process.

An optional embodiment of a fluid collection and/or testing device can optionally collect fluids from the of the person being tested by absorption driven by capillary forces native to the specified absorptive materials, wherein the device can optionally have an indicator that changes color or provides an visual, mechanical, or electrical indicator when the device is full of; or has sufficient, fluid to conduct the selected test. This indicator can also serve as a passive timer for chemically conditioning the fluid since dissolution of the dried chemicals and/or action of these chemicals on the components of the fluid is not an instantaneous process and/or can require some time to optimally condition the fluid. As opposed to the person supervising the testing conducting or providing the timing the fluid conditioning portion of the process, this functionality can optionally be included as a feature of the testing device itself. This timing can be varied, as a non-limiting example, by changing the distance of migration or the materials supporting migration to reach an optimal time for conditioning.

Sample entry control and preparation, flow control, and venting. A feature of the testing device, as provided in non-limiting optional embodiments, is that introduction of the unconditioned fluid to the lateral flow test strips can optionally not occur until sufficient incubation time has elapsed and/or a label or sticker is removed from the device. As the device is filling with or collecting fluid, the fluid can enter a region containing conditioning chemicals and/or buffers. A testing device can optionally contain one or more capillary force based and/or shaped compartments, that can optionally be functionally air tight from the outside environment when fluids are introduced to the device, optionally unless a vent is added, provided, or activated, such as with vent holes provided in the device, which can optionally be shut off by fluid movement to predetermined locations in the device. In order for fluid to optionally flow into the materials included in each compartment, a vent to the outside can optionally be present to allow air displacement by the entering fluid. If the vent isn't present, fluid may optionally not enter the compartment by capillary forces alone. By placing a removable sticker over the vent of the chamber(s) containing the later flow test strips, the user can optionally control when the fluid enters this chamber. In one embodiment, the testing initiation sticker covering the vent for the test strip chamber can optionally only be removed when the device indicates sufficient fluid has been collected and/or because of the preset passive timing aspects that are optionally designed into the fill indicator, when sufficient time has elapsed for the fluid to be conditioned, which was in contact with the conditioning chemicals before the fill indicator indicated "full" and/or would then be in an optimal state for lateral flow testing.

Optional functions of non-limiting optional embodiments can include one or more of:
1. Collection of bodily fluids and/or ensuring that the filling of the internal compartments of the testing device only occurs through capillary forces generated by the liquid interacting with the transport materials incorporated within the device. No test subject generated pressure of vacuum effects.
2. Ensuring that the fluid spends a set or minimum time with the fluid conditioning chemicals.
3. A fill indicator can optionally serve two purposes.
   a. Indicate that sufficient fluid has been collected to ensure that the device has sufficient sample to complete testing.
      i. A time required to fill is optionally and not directly related to the time it takes for the indicator to indicate a full state. An observed fill time can be artificially extended to ensure that fluid has incubated with the conditioning chemicals a sufficient amount of time. This can optionally be accomplished by the choice of materials in the fill indicating area since these can be chosen based on lateral flow rates thus impacting the observed fill time. This can also be optionally accomplished by simply lengthening the migration distance of the fluid in the fill indicator area to modify the observed fill time.
4. An optional removable label or incorporated vent hole can when present prevent the flow of fluid onto the later flow test strip and/or permit the flow of fluid onto the lateral flow test strips when removed opened or closed.
   a. Controlling fluid flow rates in the lateral flow testing devices. A precise nature of the laminated structure can apply very precise pressure to the reagent test strip or pads of the lateral flow test strip thus compressing the pad slightly but limiting the amount of compression and/or slowing and/or the flow rates into the lateral flow test strip providing more time and/or optimization for indicator reactions to occur.
   b. Flow rates within lots of test strips can be variable due to variable densities of reagent pads. Compressing these pads to the same height with a limited and/or precise amount of volume compression has been discovered to improve flow rate consistency, optionally using surfactants in the strip or pad.

The test strip can optionally analyze the presence or amount of an EtG ethanol metabolite thereof in a bodily fluid or tissue to determine whether said amount is above a pre-selected threshold or concentration, or to provide a reading of result 8 quantitatively or qualitatively.

The term "component" can refer, but is not limited to designated selected regions, such as edges, corners, sides or the like; structural members, such as strips, pads, layers or panels, layers of material, or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a test strip that is placed with or near the element, formed or applied within a layer of the element or another test strip, or other variations or combinations thereof.

The various parts of the test strip can be attached to one another or associated with one another to form a structure that preferably maintains its shape during the useful life of the test strip. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the test strip to one another.

Ethyl Glucuronide Immunogens

Implementing an immunoassay for the detection of a small molecule, such as EtG, can be a challenge. This is because such small molecules can often lack antigenicity, making it difficult to generate antibodies. It is particularly problematic with EtG, which lacks immunogenicity. To increase the immunogenicity, larger antigenic compounds including, but not limited to, BSA, ovalbumin, KLH, and the like, can be coupled to EtG. Further, detection of EtG in an immunoassay generally requires the use of a detectable tracer conjugated to an antibody, EtG, or EtG analog.

Accordingly, coupling an immunogenic operative moiety to EtG can provide an EtG immunogen that is sufficiently immunologically similar to EtG so that antibodies induced by the immunogen can react with the immunogen, EtG, and other EtG analogs. As such, an immunogen based on EtG is also considered an EtG analog. EtG analogs in accordance with the present invention which include an immunogenic carrier can be capable of inducing the production of anti-EtG antibodies, such as monoclonal and polyclonal antibodies. Accordingly, the antibodies generated using unique EtG immunogens can interact and/or bind with EtG and other EtG analogs. These antibodies, immunogens, antigens, and analogs can be useful in preparing for and performing immunoassays for the detection of EtG in biological samples.

Immunogens can be made by coupling EtG to an immunogenic or antigenic carrier protein through a linker at either the 1-carbon or 5-carbon position of the glucyl ring of EtG or an EtG analog. Also, it has been found in some instances that longer linkers can increase the affinity of the antibodies produced. In part, it is thought, without being bound thereto, that longer linkers can allow more accessibility to the antigen. Also, due to the increased surface area of the exposed antigen or epitope, the avidity may also be increased, providing an improvement in the art.

An immunogenic moiety can include various proteins or polypeptides, which can function as an immunogenic carrier. These types of polypeptides include albumins, serum proteins, globulins, ocular lens proteins, lipoproteins, and portions thereof. Illustrative proteins include BSA, KLH, egg ovalbumin, bovine gamma-globulin ("BGG"), and the like. Alternatively, synthetic polypeptides may be utilized. Additionally, an immunogenic moiety can also be a polysaccharide, which is a high molecular weight polymer. Examples of polysaccharides are starches, glycogen, cellulose, carbohydrate gums such as gum arabic, agar, and the like. Also, an immunogenic moiety can be a polynucleotide, such as DNA or RNA. The polynucleotide can be modified or unmodified, and comprised of any number of nucleic acids so long as it provides the carrier and/or immunogenic functionality. The polysaccharide can also contain or link to a polypeptide residue, polynucleotide residue, and/or lipid residue. Furthermore, an immunogenic moiety can either be a polynucleotide alone or conjugate to one of the polypeptides or polysaccharides mentioned above.

An immunogenic moiety or carrier can also be a particle or microparticle. The immunogenic particles are generally at least about 0.02 microns ($\mu$m) and not more than about 100 $\mu$m, and usually about 0.05 $\mu$m to 10 $\mu$m in diameter. The particle can be organic or inorganic, swellable or non-swellable, and/or porous or non-porous. Optionally, an immunogenic particle can have a density approximating water, generally from about 0.5 to 1.5 g/mL, and be composed of a material that can be transparent, partially transparent, or opaque. The immunogenic particles can be biological materials such as cells and microorganisms, including non-limiting examples such as erythrocytes, leukocytes, lymphocytes, *Streptococcus*, *Staphylococcus aureus*, *E. coli*, and viral particles. The particles can also be comprised of organic and inorganic polymers, liposomes, latex, phospholipid vesicles, liposomes, cationic liposomes, anionic liposomes, lipoproteins, lipopolymers, and the like.

Optional embodiments of the present invention can include one or more EtG immunogens for generating EtG antibodies, wherein be an EtG analog for use in a process for preparing and/or implementing an immunoassay for detecting EtG in a sample. Such an EtG analog can be prepared in accordance with Formula (I): -[-EtG-L-X—Y-]n-Z. In accordance with the formulas, the EtG analog can be characterized as follows: n can be greater than or equal to 1 and/or less than about 1000; L can be at least one of the groups 0, S, CO, COO, $SO_2$, $CH_2$, NH, $NH(CH_2)_2NH$, CONH, Ph, $NHCH_2Ph$, or the like; X can be at least one of a bond between L and Y, an aromatic group, or an aliphatic group; Y can be selected from the group consisting of aliphatic, alcohol, amine, amide, carboxylic acid, aldehyde, ester, activated ester, aliphatic ester, imidoester, isocyanate, isothiocyanate, anhydride, thiol, thiolactone, diazonium, maleimido, NHS, O—NHS, and a linker derived therefrom coupled with an operative moiety; and Z can be an operative moiety.

In non-limiting embodiments, X can be at least one of a bond between L and Y, a substituted or unsubstituted aromatic or aliphatic group having from 1 to 2 rings, or a saturated or unsaturated, substituted or unsubstituted, and straight or branched chain having from 1 to 20 carbon and/or hetero chain atoms. Also, when used, the operative moiety Z can be selected from the group consisting of proteins, lipoproteins, glycoproteins, polypeptides, poly(amino acids), polysaccharides, nucleic acids, polynucleotides, teichoic acids, detectable labels, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, albumin, human serum albumin, bovine serum albumin, keyhole limpet hemocyanin, and combinations thereof. In the instance the analog is an immunogen, Z can be at least one of the following: human serum albumin with n being about 1 to about 35; bovine serum albumin with n being about 1 to about 35; or keyhole limpet hemocyanin with n being about 1 to about 500. In the instance the analog is an immunoassay reagent for detecting EtG, Z can be a detectable label. For example, the detectable label can be an enzyme (e.g., Glucose-6-phosphate dehydrogenase "G6PDH"), enzyme fragment, or enzyme donor fragment (e.g., beta-galactosidase enzyme donor fragment ED28).

Thus, the immunogens prepared in accordance with the present invention can be used to generate antibodies that can have an affinity for EtG as well as EtG analogs.

Anti-EtG Antibodies

In non-limiting embodiments, an EtG analog-based immunogen in accordance with the present invention can be used in an embodiment of a method for producing monoclonal and/or polyclonal antibodies. As such, antibodies can be produced from the EtG-based immunogen and interact and/or bind with EtG. Also, methods of producing antibodies with immunogens are well known in the art. The immunogens can be used in the screening for the monoclonal and/or polyclonal antibodies that interact and/or bind with EtG.

For example, a well-known method for obtaining antibodies can be utilized with an EtG-based immunogen in order to prepare anti-EtG antibodies. As such, an immunogen based on an EtG or an EtG analog can be obtained and combined with an immunogenic formulation. Briefly, about 0.5 mL of an immunogenic composition is admixed with about 0.5 mL of complete Freund's adjuvant; however, other amounts of immunogen and/or adjuvant can be used. The immunogenic formulation can then be administered to an antibody producing subject, which can be a rat, mouse, pig, rabbit, bird, sheep, and/or other animal, but preferably a mammal. The administration can be via tail vein injection, subcutaneous injection, intravenous injection, or other well-known injection sites. Subsequently, immunogenic boosters can be administered to the animal that received the initial administration, wherein the booster can include substantially the same ingredients as the initial formulation and can be administered at predetermined intervals. For example, the initial administration can be followed by subsequent boosters once a week or at other longer or shorter intervals. After at least the initial administration, and optionally after subsequent boosters, the anti-EtG antibodies produced by the animal can be collected. The antibodies can be collected by obtaining blood, serum, plasma, or other biological sample from the animal previously administered the immunogen. Optionally, the antibody-containing composition can then be processed as is well known in the art, wherein such processing can include techniques that place the antibodies into a format suitable for performing an immunodiagnostic assay. Alternatively, the processing can include screening the antibodies with ELISA by well-known and established techniques. Additionally, the processing can be used to obtain polyclonal antibodies as is well known in the art.

Test Strip Features and Components: A lateral flow testing device of non limiting optional embodiments made according to the invention can be of any shape and dimensions, such as one or a combination of square, round, oval, polygonal, hexagonal, and the like, but preferably is a rectangular test strip.

A test strip of a test device of the non-limiting optional embodiments made according to the invention may comprise as comprising the substrate, at least in part, any bibulous or non-bibulous material, such as nitrocellulose, nylon, paper, glass fiber, dacron, polyester, polyEthylene, olefin, or other cast or thermoplastic materials such as polyvinyl chloride, polyvinyl acetate, copolymers of vinyl acetate and vinyl chloride, polyamide, polycarbonate, polystyrene, etc. In a preferred embodiment, at least one test strip material is nitrocellulose having a pore size of at least about 1 micron, more preferably of greater than about 5 microns, or about 8-12 microns. Suitable nitrocellulose sheets having a nominal pore size of up to approximately 12 microns, are available commercially from, for example, Schleicher and Schuell GmbH.

A test strip used in context with the non-limiting optional embodiments can optionally include indicia that can include a designation for the test to be performed using the test strip. Such indicia may be printed on the test strip material using methods known in the art. Alternatively, indicia may be on other thin members, such as plastic or paper, that are attached to the test strip, such as by adhesives.

A test strip can include one or more materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another.

A material or materials of the test strip can be bound to a support or solid surface such as found, for example, in thin-layer chromatography and may have an absorbent pad either as an integral part or in liquid contact. For example, a test strip may comprise nitrocellulose sheet "backed", for example with a supporting sheet, such as a plastic sheet, to increase its handling strength. This can be manufactured by forming a thin layer of nitrocellulose on a sheet of backing material. The actual pore size of the nitrocellulose when backed in this manner will tend to be lower than that of the corresponding unbacked material. Alternatively, a preformed sheet of nitrocellulose and/or one or more other bibulous or non-bibulous materials can be attached to at least one supporting sheet, such as a sheet made of polymers (see, e.g., U.S. Pat. No. 5,656,503, entirely incorporated by reference). A supporting sheet can be transparent, translucent or opaque. In aspects of the non-limiting optional embodiments where the support sheet is transparent, the supporting sheet is preferably moisture impervious but can be moisture resistant or moisture pervious. In the non-limiting optional embodiments the test strip can be viewed through a window comprised of a transparent material such as glass, plastic, or mylar, but preferably break resistant.

In the following discussion strips of test strip material will be described by way of illustration and not limitation.

Generally, test strips of the non-limiting optional embodiments include a sample application zone and a test results determination region. A test results determination region can include either or both of one or more EtG ethanol metabolite detection zones and one or more control zones. Optionally, a test strip can include a reagent zone.

One or more specific binding members in the test results determination region of the test strip can be impregnated throughout the thickness of the substrate as a bibulous or non-bibulous material in the test results determination region (for example, specific binding members for one or more drugs, compound, or metabolite can be impregnated throughout the thickness of the test strip material in one or more EtG ethanol metabolite detection zones, and specific binding members for one or more EtG ethanol metabolites can be impregnated throughout the thickness of the test strip material in one or more control zones, but that need not be the case). Such impregnation can enhance the extent to which the immobilized reagent can capture an EtG ethanol metabolite present in the migrating sample. Alternatively, reagents, including specific binding members and components of signal producing systems may be applied to the surface of the bibulous or non-bibulous material. Impregnation of specific binding members into test strip materials or application of specific binding members onto test strip materials may be done manually or by machine.

Nitrocellulose has the advantage that a specific binding member in the test results determination zone can be immobilized without prior chemical treatment. If the porous solid phase material comprises paper, for example, the immobilization of the antibody in the test results determination zone can be performed by chemical coupling using, for example, CNBr, carbonyldiimidazole, or tresyl chloride.

Following the application of a specific binding member to the test results determination zone, the remainder of the porous solid phase material should be treated to block any remaining binding sites elsewhere. Blocking can be achieved by treatment with protein (for example bovine serum albumin or milk protein), or with polyvinylalcohol or ethanolamine, or any combination of these agents. A labeled reagent for the reagent zone can then be dispensed onto the dry carrier and will become mobile in the carrier when in the moist state. Between each of these various process steps (sensitization, application of unlabeled reagent, blocking and application of labeled reagent), the porous solid phase material should be dried.

To assist the free mobility of the labeled reagent when the test strip is moistened with the sample, the labeled reagent can be applied to the bibulous or non-bibulous material as a surface layer, rather than being impregnated in the thickness of the bibulous material. This can minimize interaction between the bibulous or non-bibulous material and the labeled reagent. For example, the bibulous or non-bibulous material can be pre-treated with a glazing material in the region to which the labeled reagent is to be applied. Glazing can be achieved, for example, by depositing an aqueous sugar or cellulose solution, for example of sucrose or lactose, on the carrier at the relevant portion, and drying (U.S. Pat. No. 5,656,503). A labeled reagent can then be applied to the glazed portion. A remainder of the carrier material should not be glazed.

Reagents can be applied to the carrier material in a variety of ways. Various "printing" techniques have previously been used or known in the art for application of liquid reagents to carriers, for example micro-syringes, pens using metered pumps, direct printing and ink-jet printing, and any of these techniques can be used in the present context. To facilitate manufacture, the carrier (for example sheet) can be treated with the reagents and then subdivided into one or more of smaller portions, layers, components, laminates, or other structures (for example small narrow strips each embodying the required reagent-containing zones) to provide a plurality of identical carrier units.

In embodiments where the EtG is detected by a signal producing system, such as by one or more enzymes that specifically react with the analyte, one or more components of the signal producing system can be bound to the EtG detection zone of the test strip material in the same manner as specific binding members are bound to the test strip material, as described above. Alternatively or in addition, components of the signal producing system that are included in the sample application zone, the reagent zone, or the EtG detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the EtG detection zone of the test strip, or that are included throughout the test strip, may be applied to the surface of one or more test strip materials of the test strip as was described for labeled reagents.

Sample Application Zone

A sample application zone is an area of a test strip where a sample, such as a fluid sample, such as a biological fluid sample such as blood, serum, saliva, or urine, or a fluid derived from a biological sample, such as a throat or genital swab, is applied. A sample application zone can include a bibulous or non-bibulous material, such as filter paper, nitrocellulose, glass fibers, polyester or other appropriate materials. One or more materials of the sample application zone may perform a filtering function, such that large particles or cells are prevented from moving through the test strip. A sample application zone can be in direct or indirect fluid communication with the remainder of the test strip, including the test results determination zone. A direct or indirect fluid communication can be, for example, end-to-end communication, overlap communication, or overlap or end-to-end communication that involves another element, such as a fluid communication structure such as filter paper.

A sample application zone or other part of the substrate can also optionally include compounds or molecules that may be necessary or desirable for testing and/or optimal performance of the test. The sample application zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

Reagent Zone

A test strip can also include a reagent zone where reagents useful in the detection of an EtG ethanol metabolite can be provided immobilized (covalent or non-covalent immobilization) or not immobilized, particularly when in a fluid state. A reagent zone can be on a reagent pad, a separate segment of substrate, e.g., comprising a bibulous or non-bibulous material included on the test strip, or it can be a region of a bibulous or non-bibulous material of a test strip that also includes other zones, such as an EtG ethanol metabolite detection zone. In one aspect of non-limiting optional embodiments, the reagent zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

In one example, the reagent zone can include two or more populations of colored beads. One population of colored beads is attached to an anti-rabbit IgG antibody or active fragment thereof and the other population of colored beads is attached to an anti-EtG ethanol metabolite antibody or active fragment thereof. A labeled anti-rabbit IgG antibody or antibody fragment is used for visual detection of a signal in the control zone of the test strip. A color signal in the control zone indicates that the sample has passed through the detection zone. A labeled anti-EtG ethanol metabolite antibody or fragment thereof provides a visual signal in the detection zone indicating the presence of EtG ethanol metabolite in the sample.

Other preferred embodiments are having anti-(drug of abuse) antibodies or active fragments thereof bound to a population of colored beads. More than one population of beads can be used as in the forgoing example to provide a visual signal in the detection zone and a second visual signal in the control zone. The various populations of beads can be the same or are different colors or can be provided as a mixture of colors. Alternatively or in addition, different populations of beads bound to different antibodies or antibody fragments can be used to indicate the presence of more than one EtG ethanol metabolite in a sample by producing one or more visual signals in one or more detection zones. The detection zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

Preferred labels are beads such as metal particles, such as colloidal or latex gold, or polymeric beads, such as colored beads, or particles of carbon black. Other labels include, for example, enzymes, chromophores or fluorophores such as they are known in the art, particularly in immunoassays, or later developed. A population of beads are provided in powdered form on the reagent zone, which can include a bibulous material, such as filter paper, glass fibers, nylon, or nitrocellulose. These reagents are reversibly bound to the reagent zone because they can be mobilized when placed in contact with a fluid, such as a fluid sample passing along a test strip.

In another embodiment of non-limiting optional embodiments, the reagent zone can include components of a signal producing system, for example, catalysts, such as enzymes, cofactors, electron donors or acceptors, and/or indicator compounds.

A reagent zone can also include compounds or molecules that may be necessary or desirable for optimal performance of the test, for example, buffers (preferably dry buffers or conditioners), stabilizers, surfactants, salts, reducing agents, or enzymes.

Test Results Determination Zone

A test results determination zone includes immobilized or non-immobilized reagents that can detect the presence of the EtG being tested for, and antibodies. Such reagents are preferably in a dry state and can be covalently immobilized, non-covalently immobilized, or notimmobilized in a fluid state. A test result determination zone can include either or both of one or more EtG ethanol metabolite detection zones and one or more control zones.

Depending on the particular format and EtG ethanol metabolite being tested for, a variety of reagents can be provided at the test results determination zone. For example, the test results determination zone can include specific binding members such as antibodies, enzymes, enzymatic substrates, coenzymes, enhancers, second enzymes, activators, cofactors, inhibitors, scavengers, metal ions, and the like. One or more of the reagents provided at the test results determination zone can be bound to the test strip material. Test strips including such reagents are known in the art and can be adapted to the test device of the present invention.

In a preferred aspect of the present invention, the one or more medical, EtG ethanol metabolite detection zones of the test results determination zone include one or more immobilized (covalently or non-covalently immobilized) specific binding members that bind with the EtG, as bound by specific binding members bound to a label as are provided in the reagent zone. Thus, in embodiments where the reagent zone contains one or more specific binding members for the analyte, the specific binding members of the reagent zone and EtG ethanol metabolite detection zone should bind with different epitopes on the EtG ethanol metabolite being tested for. For example, when a labeled specific binding member in the reagent zone binds with the EtG, then the immobilized specific binding member in the EtG detection zone should bind with another area of the EtG ethanol metabolite. Thus, when the EtG is present in the sample, EtG will bind the labeled anti-EtG ethanol antibody, which carried along to the test result determination zone at the EtG detection zone which binds with the immobilized anti-EtG to provide a visual readout.

An EtG detection zone can include substrates which change in an optical property (such as color, chemiluminescence or fluorescence) when an EtG ethanol metabolite is present. Such substrates are known in the art, such as, but not limited to, 1,2-phenylenediamine, 5-aminosalicylic acid, 3,3',5,5'tetra methyl benzidine, or tolidine for peroxidase; 5-bromo-4-chloror-3-indolyl phosphate/nitroblue tetrazolium for alkaline phosphatase and 5-bromo-4-chloro-3-indolyl-beta-D-galactopyranoside, o-nitrophenyl-beta-D-galactopyranoside, napthol-AS-BI-beta-D-galactopyranoside, and 4-mEthyl-umbelliferyl-beta-D-galactopyranoside for beta galactosidase.

In embodiments where EtG is detected by a signal producing system, one or more components of the signal producing system, such as enzymes, substrates, and/or indicators, can be provided in the EtG detection zone. Alternatively, the components of the signal producing system can be provided elsewhere in the test strip and can migrate to the EtG detection zone.

Optionally, the test results determination zone can include an optional control zone. A control zone can be upstream from, downstream from, or integral with the EtG detection zone of the test result determination zone. In the latter case, when EtG ethanol metabolite and control give a positive reaction, the control zone and/or EtG ethanol metabolite detection zone can form an indicia, such as a colored bar, marking, indicator, or "+" sign for a positive reaction and a colored bar, marking, indicator, "−" sign for a negative reaction based on the particular format of the assay, and the assay test strip or case or casing can also optionally include an indication or indication area that indicates that the one or more of the assays is not valid, either as the test or the control, optionally as a negative or positive control for one or more the assays as run on one or more of the test strips.

A control zone provides a result that indicates that the test on the test strip has performed correctly. In one preferred aspect of the present invention, the reagent zone includes a specific binding member that binds with a known EtG ethanol metabolite different from the EtG being tested for. For example, a rabbit-IgG may be provided in the reagent zone. A control zone can include immobilized (covalently or non-covalently) anti-rabbit-IgG antibody. In operation, when the labeled rabbit-IgG in the reagent zone is carried to the test result determination zone and the control zone therein, the labeled rabbit-IgG will bind with the immobilized an anti-rabbit-IgG and form a detectable signal.

A control zone can include substrates which change in an optical property (such as color, chemiluminescence or fluorescence) when an optional substance is present.

In one preferred aspect of the present invention, the test strip can include a results determination zone that includes an optional and an EtG ethanol metabolite detection zone, and a sample adulteration control zone. In another aspect of the present invention, a test strip can include a results determination zone that optionally includes an optional, and optionally an adulteration control zone. A second test strip can include an adulteration control zone and optionally an optional. Preferably, this second test strip includes both an adulteration control zone and an optional, but that need not be the case. In the instance where one or more first test strips can be used to detect an EtG ethanol metabolite other than an adulteration EtG ethanol metabolite and one or more second test strips can be used to detect an adulteration analyte, the test strips can be provided as multiple test strips or test strips that detect multiple drugs, compounds or metabolites.

Orientation of Zones

Various zones of a test strip, including a sample application zone, one or more reagent zones, and one or more test result determination zones, including one or more EtG ethanol metabolite detection zones and optionally including one or more control and one or more adulteration zones, can be on a single strip of material, such as filter paper or nitrocellulose, or can be provided on separate pieces and/or layers of material. Different zones can be made of the same or different material or a combination of materials, but preferably are selected from bibulous materials, such as filter paper, fiberglass mesh and nitrocellulose. A sample application zone preferably includes glass fibers, polyester or filter paper, the one or more reagent zones preferably include glass fibers, polyester or filter paper and the test results determination zone, including one or more EtG ethanol metabolite detection zones and optionally including one or more control, preferably include nitrocellulose.

Optionally, a fluid absorbing zone is included. A fluid absorbing zone preferably includes absorbent paper and is used to absorb fluid in a sample to drive fluid from the sample application zone through the reagent zone and the detection zone, which can optionally also include dry buffers or conditioning compositions.

Preferably, the zones are arranged as follows: sample application zone, one or more reagent zones, one or more test results determination zones, one or more control, one or more adulteration zones, and fluid absorbing zone. If the test results determination zone includes an optional, preferably it follows the EtG detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such an adjoining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip includes an adulteration control zone, the adulteration control zone can be placed before or after the results determination zone. When an optional adulteration control zone is present in the results determination zone on such a test strip, then the adulteration control zone is preferably before the control zone, but that need not be the case. In non-limiting optional embodiments where a test strip is an optional test strip for the determination of an adulteration EtG ethanol metabolite and/or an optional, then the adulteration control zone can be placed before or after the control zone, but is preferably before the control zone.

Methods of Detecting of an EtG Ethanol Metabolite in a Sample

A device of non-limiting optional embodiments can be used to collect a sample, transfer the sample to a test strip sample receiving zone and optionally mix the sample with one or more reagents, such as dry buffer or conditioner. A sample or sample and one or more reagents can then be conducted to a test element within a test strip to detect one or more drugs, compounds, or metabolites in the sample, preferably a sample application zone of a test strip. A sample can be liquid or colloidal. Examples of liquid or fluid samples that can be applied to the test strip can include blood, serum, saliva, or urine.

To collect a sample, a fluid or colloidal sample can be applied via various techniques, for example pipeting, pouring or by use of a dropper. Alternatively, a sample collection device can be used to collect a sample and transfer the sample onto the test strip. A sample collection device can be of different structures but is preferably a swab. A swab can be used to collect the sample onto the swab head by different embodiments such as for example dipping, swiping or swabbing. A swab with sample can be applied to the test strip that can optionally contain one or more reagents, or with dry buffer added to the sample.

Non limiting optional embodiments optionally provides a portable drug testing platform for digital image capture and analysis of pre-calibrated/quantitation of lateral flow drug test strips using dry buffer or pre-conditioning of saliva or body fluid test samples. A platform can optionally include digital camera hardware with digital components that record the pre-calibrated/quantitative test strips optionally including active chemistry and specific for one or more drugs, compounds, or metabolites; dry buffer or conditioning media for preparing the test sample; software for interfacing with the user, and an image processing and computing device to interface with the digital camera.

In the particular embodiment, the system accepts a broad range of lateral flow testing devices. A test sample (e.g., saliva or body fluid) is taken from the person being tested and added to one or more of the test cartridge or the test strip, that is provided with dry buffer or conditioners to set up the sample for addition to the test strip for testing. A lateral test strip or test cartridge is provided with the conditioned test sample at a designated area and the sample then continues by timing or indicator to the designated or proper position for interaction with the drug analysis components of the test strip to react the sample to provide the indication of a positive, negative, and/or threshold amount of the EtG being tested by a particular test strip. A test strip or casing of the test strip is provided with calibration, sufficient test sample, and result indicator markings to show the result of the test for each test strip and corresponding drug, compound or metabolite being tested.

A system then continues the drug testing by taking a digital image of the sample conditioned and run on each test strip with the digital camera positioned, optionally, via the tester, case and/or housing. Illumination can optionally be provided by the digital camera or a separate illumination source. Digital image data of the test strip result, additional identifying information including one or more of identification of the person being tested, information about the tester, the location, the drug testing being done, and the like, and this image and other data is collected and stored in the digital camera, data memory storage, and/or a cloud based or separate data memory storage device. A digital image data is then processed using a host device (e.g. dedicated smart phone, PDA, laptop, cellular phone, or the like) using processing capabilities in conjunction with the software component of the system. Software pre-loaded onto the smart phone or processor provides the processing instructions and compares image analysis data to pre-defined calibration data, yielding a qualitative or quantitative result, e.g., but not limited to positive, negative, over or below one or more threshold concentrations or amounts, and the like. A system can interface with the host device through several different physical standards. These standards include industry standards such as Personal Computer Memory Card International Association (PCMCIA), Universal Serial Bus (USB), Serial, Secure Digital, Bluetooth™, one or a combination of optical, magnetic, or solid state data drives, Wi-Fi or other company specific standards such as the Handspring Springboard Platform™.

In another embodiment, software is automated for later flow test strip digital imaging for cross-field testing compatibility. This system can provide compatibility with a wide array of commercial or custom lateral flow strips. A system digitizes and objectively quantifies results from tests (such as test strips that can optionally be conventionally read by a human manually); stores original and modified digital image and data into memory for review; and enhances test processing by executing image processing algorithms.

Immunodiagnostic Assays

The anti-EtG antibodies, either monoclonal or polyclonal, can be used in immunoassays for identifying the presence of EtG in a sample, such as blood, plasma, serum, tissue, and the like. This can be beneficial for identifying or determining whether or not a subject has ingested alcoholic beverages. Thus, the anti-EtG antibodies can be used in immunodiagnostic assays in place of other antibodies so that the assays can be configured for identifying the presence and optionally quantifying the amount of EtG, which is an indication of alcohol consumption. Additionally, the immunodiagnostic assays can use EtG analogs in accordance with the present invention or other EtG analogs.

The EtG antibodies described herein are also suitable for any of a number of heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the EtG analogs, conjugates, antibodies, immunogens and/or tracers, such assays can also be modified as is well known in the art. As such, various modifications of steps or acts for performing such immunoassays can be made within the scope of the present invention.

EXAMPLES

The following examples are provided to illustrate embodiments of the invention and are not intended to be limiting. Accordingly, some of the examples have been performed via experiment and some are prophetic based on techniques, standards, and results well known in the art. Also, it should be apparent that the invention can optionally include additional embodiments not illustrated by example. Additionally, many of the examples have been performed with experimental protocols well known in the art using the EtG analogs, antigens, immunogens, and anti-EtG antibodies prepared in accordance with the present invention.

Example 1

Preparation of Anti-EtG Antibodies

As discussed above, any number of established procedures may be used to prepare antibodies using an immunogen as described above. For example, the immunogen shown in FIG. 2A-C, in Freund's adjuvant, was used to immunize mice. Following a series of immunizations, as routine in the art, the spleens were removed and fused with an immortal non-producing myeloma cell line to produce hybridoma cell lines using methods known in the art. For the purposes of the present invention, various hybridoma cell lines (e.g., 19D7, 14C5, and 12E7 clones) were selected for production of monoclonal antibodies, after preliminary screening of culture supernatant for capacity to recognize EtG. Although several hybridoma cell lines showed positive reactivity when screened against EtG, hybridoma cell lines 19D7, 14C5, and 12E7 clones, were selected for a variety of reasons, including its growth and antibody production characteristics.

Example 2

Detection of EtG from Urine

Ethyl Glucuronide (EtG) is a Minor Nonoxidative Metabolite of Ethyl Alcohol Formed by the in vivo conjugation of ethanol with glucuronic acid with UDP glucuronosyl transferase. ETG is a product of the metabolic process of ingested alcohol (ethanol), which is rapidly metabolized in the body, and which is also excreted in the blood, hair and urine. By using an ETG Rapid Test Device, ETG can be detected in the urine, confirming the consumption of alcohol. The ETG metabolite remains in the body longer and therefore has a more useful window of detection of 8 to 80 hours. ETG testing according the invention is an excellent option, e.g., but not limited to, zero-tolerance alcohol consumption or rehabilitation programs.

A non limiting embodiment of the invention can include an EtG lateral flow immunoassay test strip and/or device, e.g., an ETG Rapid Test Device (Urine) that was designed to detect ETG through visual interpretation of color development in the Device which detection is mediated by the use of EtG specific antibodies that have been labeled for detection. The membrane or similar component of the test strip can be immobilized with ETG conjugates on the test region, and the sample pad pre-coated with colored or labeled anti-ETG antibodies, e.g., but not limited to, colloidal or latex gold labeled EtG antibody (e.g., monoclonal or polyclonal, or an EtG binding fragment thereof) conjugates. After specimens were added, (e.g., urine and controls, e.g., positive and/or negative controls) the gold conjugates moved along the membrane or test strip (e.g., chromatographically by capillary action) and the antibodies migrate to the test region. If there is no drug molecule (i.e., EtG) in the urine, then the antibody-gold conjugate attaches to the drug conjugate to form a visible line in the test region, where the formation of a visible precipitant in the test region occurs when the urine is negative for the drug. If ETG is present in the urine, the drug antigen competes with the immobilized drug conjugate on the test region for limited antibody sites. In case of sufficient concentration of the drug metabolite EtG, it fills the limited antibody binding sites. This will prevent attachment of the colored antibody-colloidal or latex gold conjugate to the drug conjugate zone on the test region. Therefore, absence of the colored band on the test region indicates a positive result. Appearance of a colored band at the control region serves as a procedural control. This indicates that proper volume of specimen has been added and membrane wicking has occurred.

During testing, a portion of the urine specimen migrates upward (or laterally) by capillary action. EtG, if present in the urine below its cut-off concentration, will not saturate the binding sites of its specific antibody. The antibody will then react with the drug-protein conjugate and a visible colored line will show up in the test line region of the specific drug strip. The presence of drug above the cut-off concentration in the urine or oral fluid specimen will saturate all the binding sites of the antibody. Therefore, the colored line will not form in the test line region. A drug-positive urine specimen will not generate a colored line in the specific test line region of the strip because of drug competition, while a drug-negative urine or oral fluid specimen will generate a line in the test line region because of the absence of drug competition.

To serve as a procedural control, a colored line will always appear at the control line region, indicating that proper volume of specimen has been added and membrane wicking has occurred.

As shown in FIG. 1, the specimen is added at the sample application region, e.g., (A), and then migrates via capillary action along the membrane or test strip to interact with the labeled conjugate (B) which can be provided in alternative labeled forms. EtG present in the specimen (e.g., urine or other bodily fluid) below cutoff or threshold amounts (e.g., less than 100, 200, 250, 300, 350, 400, 450, or 500, 600, 700, 750, 800, 900, 1000, 1100, 1200, 1300, 1400, 1500, 1700, 1750, 1800, 1900, or 2000 ng/mL), will not saturate all of the binding sites of the gold-conjugated anti-EtG antibodies and will not form a colored antibody-antigen complex (C). The gold-conjugated antibodies will then be captured by immobilized conjugate and a visible (e.g., red) band will form indicating a negative result at position (D) (corresponding to (T) in FIG. 2 below, where the gold-EtG antibody complex will bind at (D) since the EtG binding sites on the EtG antibody are not saturated and will bind EtG or epitope or a mimetic thereof immobilized at (D) to provide a labeled negative result and band at (D) (corresponding to band (T) in FIGS. 2A-C. The absence of line formation in the test line region indicates a positive reading and that the (A) level of the test specimen is above the detection sensitivity of the test (e.g., one of 100, 200, 250, 400, or 500, 600, 700, 750, 800, 900, 1000, 1100, 1200, 1300, 1400, 1500, 1700, 1750, 1800, 1900, or 2000 ng/mL, where 500, 750, or 1000 ng/mL is preferred).

In the control line region of the membrane, immobilized reagents capture colored conjugate regardless of the presence of the test specimen composition. The resulting visible red band (E) confirms that the assay is functioning correctly. FIGS. 2A-C illustrate in a non-limiting example one set of the possible outcomes of the test.

Example 3

Homogeneous Competitive Immunoassays

G6PDH-EtG conjugate is used to compete with EtG in urine, serum, or other samples for binding to an anti-EtG antibody, for example, a monoclonal antibody made according to procedures described herein. In the absence of EtG in the sample tested, the anti-EtG antibody binds to the G6PDH-EtG conjugate, inhibiting enzymatic activity. When EtG is present in a sample, it competes for binding sites on the anti-EtG antibodies, leaving at least some of the EtG-G6PDH unbound and capable of reacting with the substrate. Thus, as the concentration of EtG in a sample increases, the amount of enzymatic activity increases proportionately.

Exemplary reagents for performing such an assay include: anti-EtG antibody, which is preferably a monoclonal antibody with sensitivity and specificity specific for EtG; substrate reagent comprising 8.5 mM glucose-6-phosphate and 5.25 mM NAD in Tris buffer at pH 5.0, which can be combined with sodium azide as a preservative; enzyme conjugate reagent comprising EtG-G6PDH conjugate as described herein in Tris buffer at pH 8.0, which can be combined with sodium azide as a preservative; and calibrators, for example, different concentrations of EtG (such as 0 and 100, 200, 250, 300, 350, and/or 500, 600, 700, 750, 800, 900, 1000, 1100, 1200, 1300, 1400, 1500, 1700, 1750, 1800, 1900, or 2000 ng/mL) in a buffer or urine-buffer solution or other buffered solution suitable for use with the particular sample type to be tested, at pH 6.0. Preferably, the anti-EtG antibody is mixed into the substrate reagent. The above reagents may be packaged together as a kit with or without the calibrators, which may be packaged separately.

A calibration curve is established using, for example, Hitachi analyzer (917 or 717 or Olympus AU 640), or other comparable instrument. To use the Hitachi 917 analyzer, 35 microliters of calibrator is mixed with 80 microliters of substrate reagent containing anti-EtG antibodies and 80 microliters of enzyme conjugate reagent. To use the Hitachi 717 instrument, 20 microliters of calibrator is added to 125 microliters of substrate reagent containing anti-EtG antibodies and 125 microliters of enzyme conjugate reagent, and the instrument is used according to manufacturer's recommendations. To use the Olympus AU640 instrument, 50 microliters of calibrator is added to 80 microliters of substrate reagent containing anti-EtG antibodies and 80 microliters of enzyme conjugate reagent, and the instrument is used according to manufacturer's recommendations. When testing specimens (urine, serum, etc.), a sample of the specimen is substituted for the calibrator in the above procedures.

The following paragraphs enumerated consecutively from 1 through 12 provide for various aspects of the present invention. In one embodiment, in a first paragraph (1), the present invention provides:

1. An Ethyl glucuronide (EtG) lateral flow test strip immunoassay system for detecting Ethyl glucuronide in urine, the system comprising:
   (a) a lateral flow test strip as schematically shown in FIGS. 1 and 2A-C, the test strip comprising;
      (i) at least one type of capillary flow material capable of reproducibly providing lateral flow of a urine, bodily fluid or tissue sample through the test strip to reproducibly interact and detect EtG using a detectably labeled EtG-specific antibody and a first and a second detectable label comprised in the test strip, the system providing (1) a positive result, with a (C) colored band only developing as shown in FIG. 2B; (2) a negative result, with both the (T) colored band and a (C) colored band developing as shown in FIG. 2A; or an invalid result, with only the (T) colored band developing as shown in FIG. 2C, or no bands;
      (ii) a urine or control sample application area (A), as shown in FIG. 1, comprising a sample application component;
      (iii) a labeled EtG labeled antibody area (B), as shown in FIG. 1, comprising a detectably labeled EtG specific antibody provided in or to the test strip material, the detectably labeled EtG specific antibody comprising an EtG specific antibody conjugated to a detectable label component and soluble in or conducted along the test strip by capillary action of the urine or control sample after application to the test strip;
      (iv) a first detection area (D) comprising the first detectable label as a first labeled moiety that binds the detectably labeled EtG specific antibody, when the concentration of EtG in the urine or control sample is below a pre-selected threshold value between 100 and 2000 ng/mL; wherein the binding of the detectably labeled EtG specific antibody below the pre-selected threshold results in the negative result with both the (T) and (C) colored bands as shown in FIG. 2A; and wherein the detectably labeled EtG specific antibody does not detectably or significantly bind the first detectable label and also does not provide the negative result, when the EtG in the urine or control sample is above the pre-selected threshold value;
      (v) a second detection area (E) comprising the second detectable label as a second labeled moiety that binds the detectably labeled EtG specific antibody, when the concentration of the EtG in the urine or control sample is above the pre-selected threshold value between 100 and 2000 ng/mL; and wherein the binding of the detectably labeled EtG specific antibody above the pre-selected threshold results in the positive result with only the (C) colored band as shown in FIG. 2B; and wherein the detectably labeled EtG specific antibody does not detectably or significantly bind the first detectable label, when the EtG in the urine or control sample is above the pre-selected threshold value; and wherein, when assay is invalid, the binding of the detectably labeled EtG specific antibody results in the invalid result with only the (T) colored band as shown in FIG. 2C, or no bands; and wherein the detectably labeled EtG specific antibody does not detectably or significantly bind the second detectable label.

2. An immunoassay system as in paragraph 1, wherein the threshold is 500, 750, or 1000 ng/mL.
3. An immunoassay system as in paragraphs 1 through 2, wherein the detectable label is colloidal or latex gold.
4. An immunoassay system as in paragraphs 1 through 3, wherein the EtG specific antibody is monoclonal.
5. An immunoassay system as in paragraphs 1 through 4, wherein the affinity of the EtG specific antibody for EtG is at least $10^{-7}$ $K_D$.
6. An immunoassay system as in paragraphs 1 through 5, wherein the detectable label is comprised of an enzyme, enzyme fragment or enzyme donor fragment.
7. A method for an Ethyl glucuronide (EtG) lateral flow test strip immunoassay for detecting Ethyl glucuronide in urine, the system comprising:
   (a) providing a lateral flow test strip as schematically shown in FIGS. 1 and 2, the test strip comprising;
      (i) at least one type of capillary flow material capable of reproducibly providing lateral flow of a urine, bodily fluid or tissue sample through the test strip to reproducibly interact and detect EtG using a detectably labeled EtG-specific antibody and a first and a second detectable label comprised in the test strip, the system providing (1) a positive result, with a (C) colored band only developing as shown in FIG. 2B; (2) a negative result, with both the (T) colored band and a (C) colored band developing as shown in FIG. 2A; or an invalid result, with only the (T) colored band developing as shown in FIG. 2C, or no bands;
      (ii) a urine or control sample application area (A), as shown in FIG. 1, comprising a sample application component;
      (iii) a labeled EtG labeled antibody area (B), as shown in FIG. 1, comprising a detectably labeled EtG specific antibody provided in or to the test strip material, the detectably labeled EtG specific antibody comprising an EtG specific antibody conjugated to a detectable label component and soluble in or conducted along the test strip by capillary action of the urine or control sample after application to the test strip;
      (iv) a first detection area (D) comprising the first detectable label as a first labeled moiety that binds the detectably labeled EtG specific antibody, when the concentration of EtG in the urine or control sample is below a pre-selected threshold value between 100 and 2000 ng/mL; wherein the binding of the detectably labeled EtG specific antibody below the pre-selected threshold results in the negative result with both the (T) and (C) colored bands as shown in FIG. 2A; and wherein the detectably labeled EtG specific antibody does not detectably or significantly bind the first detectable label and also does not provide the negative result, when the EtG in the urine or control sample is above the pre-selected threshold value;

(v) a second detection area (E) comprising the second detectable label as a second labeled moiety that binds the detectably labeled EtG specific antibody, when the concentration of the EtG in the urine or control sample is above the pre-selected threshold value between 100 and 2000 ng/mL; and wherein the binding of the detectably labeled EtG specific antibody above the pre-selected threshold results in the positive result with only the (C) colored band as shown in FIG. 2B; and wherein the detectably labeled EtG specific antibody does not detectably or significantly bind the first detectable label, when the EtG in the urine or control sample is above the pre-selected threshold value; and wherein, when assay is invalid, the binding of the detectably labeled EtG specific antibody results in the invalid result with only the (T) colored band as shown in FIG. 2C, or no bands; and wherein the detectably labeled EtG specific antibody does not detectably or significantly bind the second detectable label;

applying the urine or control sample to the test strip; determining whether the urine or control sample comprises EtG above or below the threshold.

8. A method according to paragraph 7, wherein the threshold is 500, 750, or 1000 ng/mL.
9. A method according to paragraphs 7 through 8, wherein the detectable label is colloidal or latex gold.
10. A method according to paragraphs 7 through 9, wherein the EtG specific antibody is monoclonal.
11. A method according to paragraphs 7 through 10, wherein the affinity of the EtG specific antibody for EtG is at least $10^{-7}$ $K_D$.
12. An immunoassay system as in paragraphs 1 through 11, wherein the detectable label is comprised of an enzyme, enzyme fragment or enzyme donor fragment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced wit

What is claimed is:

1. An Ethyl glucuronide (EtG) lateral flow test strip immunoassay system for detecting ethyl glucuronide in a fluid sample, the system comprising:
   (a) a lateral flow test strip, the test strip comprising:
      (i) at least one type of capillary flow material capable of reproducibly providing lateral flow of the fluid sample through the test strip to reproducibly interact and detect EtG using a detectably labeled EtG-specific antibody; and a first detectable label and a second detectable label comprised in the test strip, the test strip providing:
         (1) a positive result, with a first colored band only developing;
         (2) a negative result, with both a second colored band and the first colored band developing; or
         (3) an invalid result, with only the second colored band developing or no bands;
      (ii) a sample application area, comprising a sample application component;
      (iii) a labeled EtG labeled antibody area, comprising a detectably labeled EtG specific antibody provided in or to the test strip material, the detectably labeled EtG specific antibody comprising an EtG specific antibody conjugated to a detectable label component and soluble in or conducted along the test strip by capillary action of the fluid sample after application to the test strip;
      (iv) a first detection area comprising the first detectable label as a first labeled moiety that binds the detectably labeled EtG specific antibody, when the concentration of EtG in the fluid sample is below a pre-selected threshold value between 100 and 2000 ng/mL;
      wherein the binding of the detectably labeled EtG specific antibody below the pre-selected threshold results in the negative result with both the first colored band and the second colored band; and
      wherein the detectably labeled EtG specific antibody does not detectably or significantly bind the first detectable label and also does not provide the negative result, when the EtG in the fluid sample is above the pre-selected threshold value;
      (v) a second detection area comprising the second detectable label as a second labeled moiety that binds the detectably labeled EtG specific antibody, when the concentration of the EtG in the fluid sample is above the pre-selected threshold value between 100 and 2000 ng/mL; and
      wherein the binding of the detectably labeled EtG specific antibody above the pre-selected threshold results in the positive result with only the first colored band; and
      wherein the detectably labeled EtG specific antibody does not detectably or significantly bind the first detectable label, when the EtG in the fluid sample is above the pre-selected threshold value; and
      wherein, when the assay is invalid, the binding of the detectably labeled EtG specific antibody results in the invalid result with only the second colored band, or no bands; and wherein the detectably labeled EtG specific antibody does not detectably or significantly bind the second detectable label.

2. The immunoassay system as in claim 1, wherein the threshold value is 500, 750, or 1000 ng/mL.
3. The immunoassay system as in claim 1, wherein the detectable label is colloidal or latex gold.
4. The immunoassay system as in claim 1, wherein the EtG specific antibody is monoclonal.
5. The immunoassay system as in claim 4, wherein the affinity of the EtG specific antibody for EtG is at least $10^{-7}K_D$.
6. Original) The immunoassay system as in claim 1, wherein the detectable label is comprised of an enzyme, enzyme fragment or enzyme donor fragment.
7. The immunoassay system as in claim 1, wherein the detectable label is comprised of an enzyme, enzyme fragment or enzyme donor fragment.
8. A method for an ethyl glucuronide (EtG) lateral flow test strip immunoassay for detecting ethyl glucuronide in a fluid sample above or below a threshold value, the method comprising:
   (a) providing a lateral flow test strip, the test strip comprising:
      (i) at least one type of capillary flow material capable of reproducibly providing lateral flow of a urine, bodily fluid or tissue sample through the test strip to reproducibly interact and detect EtG using a detectably labeled EtG-specific antibody; and a first detectable label and a second detectable label comprised in the test strip, the test strip providing:
- (1) a positive result, with a first colored band only developing;
- (2) a negative result, with both a second colored band and the first colored band developing; or
- (3) an invalid result, with only the second colored band developing or no bands;

(ii) a sample application area, comprising a sample application component;

(iii) a labeled EtG labeled antibody area , comprising a detectably labeled EtG specific antibody provided in or to the test strip material, the detectably labeled EtG specific antibody comprising an EtG specific antibody conjugated to a detectable label component and soluble in or conducted along the test strip by capillary action of the urine or control sample after application to the test strip;

(iv) a first detection area comprising the first detectable label as a first labeled moiety that binds the detectably labeled EtG specific antibody, when the concentration of EtG in the urine or control sample is below a pre-selected threshold value between 100 and 2000 ng/mL;

wherein the binding of the detectably labeled EtG specific antibody below the pre-selected threshold results in the negative result with both the first colored band and the second colored band; and wherein the detectably labeled EtG specific antibody does not detectably or significantly bind the first detectable label and also does not provide the negative result, when the EtG in the urine or control sample is above the pre-selected threshold value;

(v) a second detection area comprising the second detectable label as a second labeled moiety that binds the detectably labeled EtG specific antibody, when the concentration of the EtG in the urine or control sample is above the pre-selected threshold value between 100 and 2000 ng/mL; and wherein the binding of the detectably labeled EtG specific antibody above the pre-selected threshold results in the positive result with only the first colored band; and wherein the detectably labeled EtG specific antibody does not detectably or significantly bind the first detectable label, when the EtG in the urine or control sample is above the pre-selected threshold value; and wherein, when assay is invalid, the binding of the detectably labeled EtG specific antibody results in the invalid result with only the second colored band, or no bands; and wherein the detectably labeled EtG specific antibody does not detectably or significantly bind the second detectable label;

(b) applying the fluid sample to the test strip; and (c) determining whether the fluid sample comprises EtG above or below the threshold.

9. The method according to claim 8, wherein the threshold value is 500, 750, or 1000 ng/mL.

10. The method according to claim 8, wherein the detectable label is colloidal or latex gold.

11. The method according to claim 8, wherein the EtG specific antibody is monoclonal.

12. The method according to claim 8, wherein the affinity of the EtG specific antibody for EtG is at least $10^{-7}K_D$.

* * * * *